United States Patent [19]

Hughes et al.

[11] Patent Number: 4,742,818

[45] Date of Patent: May 10, 1988

[54] SOAKABLE EYEPIECE FOR ENDOSCOPES

[75] Inventors: Gregory Hughes, Westminster; Rick F. Carson, Jr., Orange, both of Calif.

[73] Assignee: Baxter Travenol Laboratories, Inc., Deerfield, Ill.

[21] Appl. No.: 920,048

[22] Filed: Oct. 17, 1986

[51] Int. Cl.$^4$ ............................................... G01B 1/06
[52] U.S. Cl. ............................................ 128/6; 128/4
[58] Field of Search ........................................ 128/4, 6

[56] References Cited

U.S. PATENT DOCUMENTS

| 3,434,775 | 3/1969 | Gosselin | 128/6 X |
| 4,273,109 | 6/1981 | Enderby | 128/6 |
| 4,341,205 | 7/1982 | Hosono et al. | 128/6 |
| 4,624,243 | 11/1986 | Lowery et al. | 128/6 |

Primary Examiner—William H. Grieb
Attorney, Agent, or Firm—Weissenberger & Peterson

[57] ABSTRACT

An eyepiece assembly for an endoscope focusable by an exterior focusing collar is made soakable by using an O ring and very fine screwthreads to prevent liquid sterilant from penetrating under the collar and entering the interior of the eyepiece. The use of an O ring also provides a uniform resistance to the turning of the focusing collar and makes the focusing adjustment shock resistant. In another aspect of the invention, the placement of the light fiber connector on the discardable stop housing improves light transmission and allows one-handed focusing of the eyepiece.

21 Claims, 4 Drawing Sheets

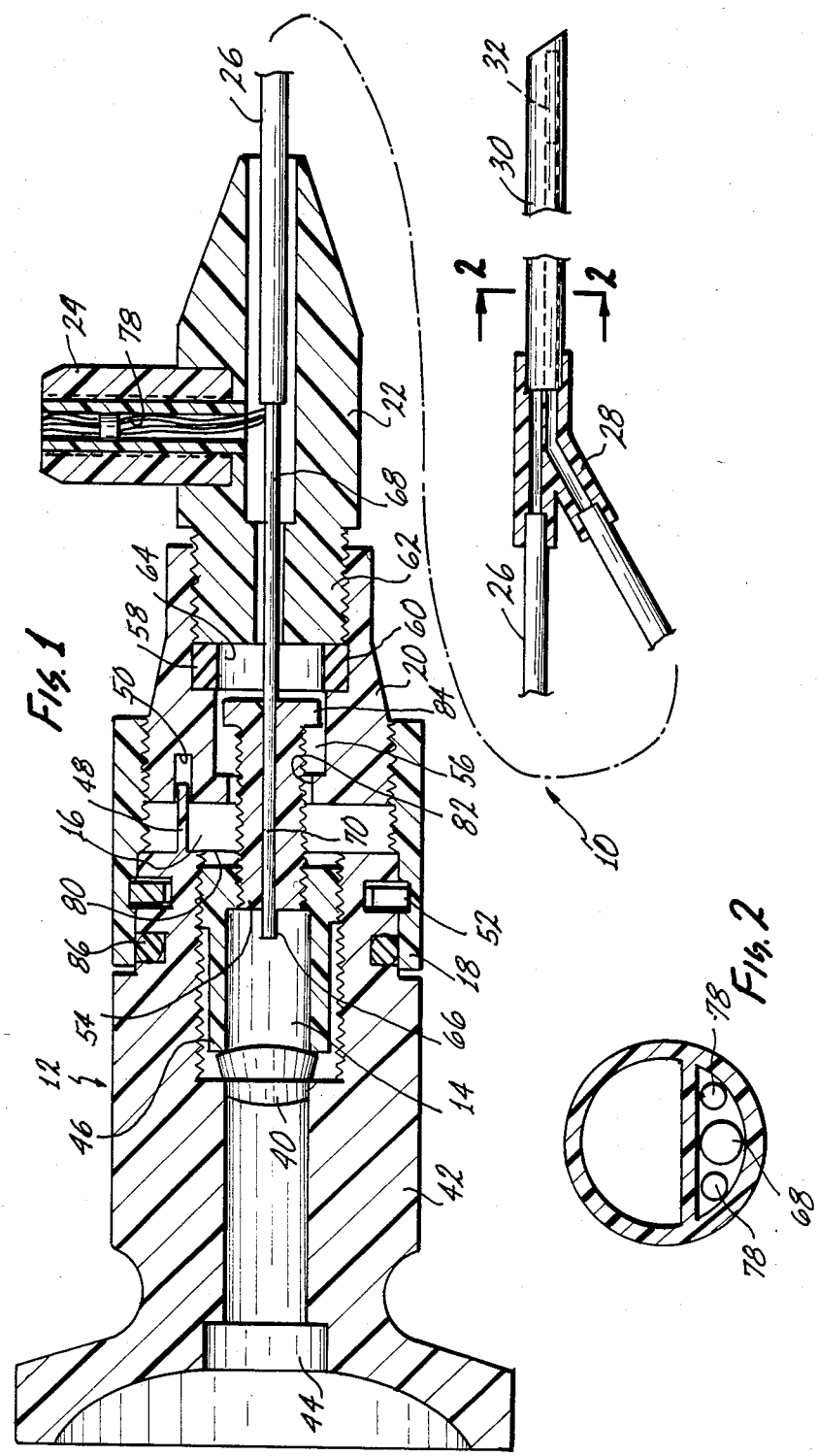

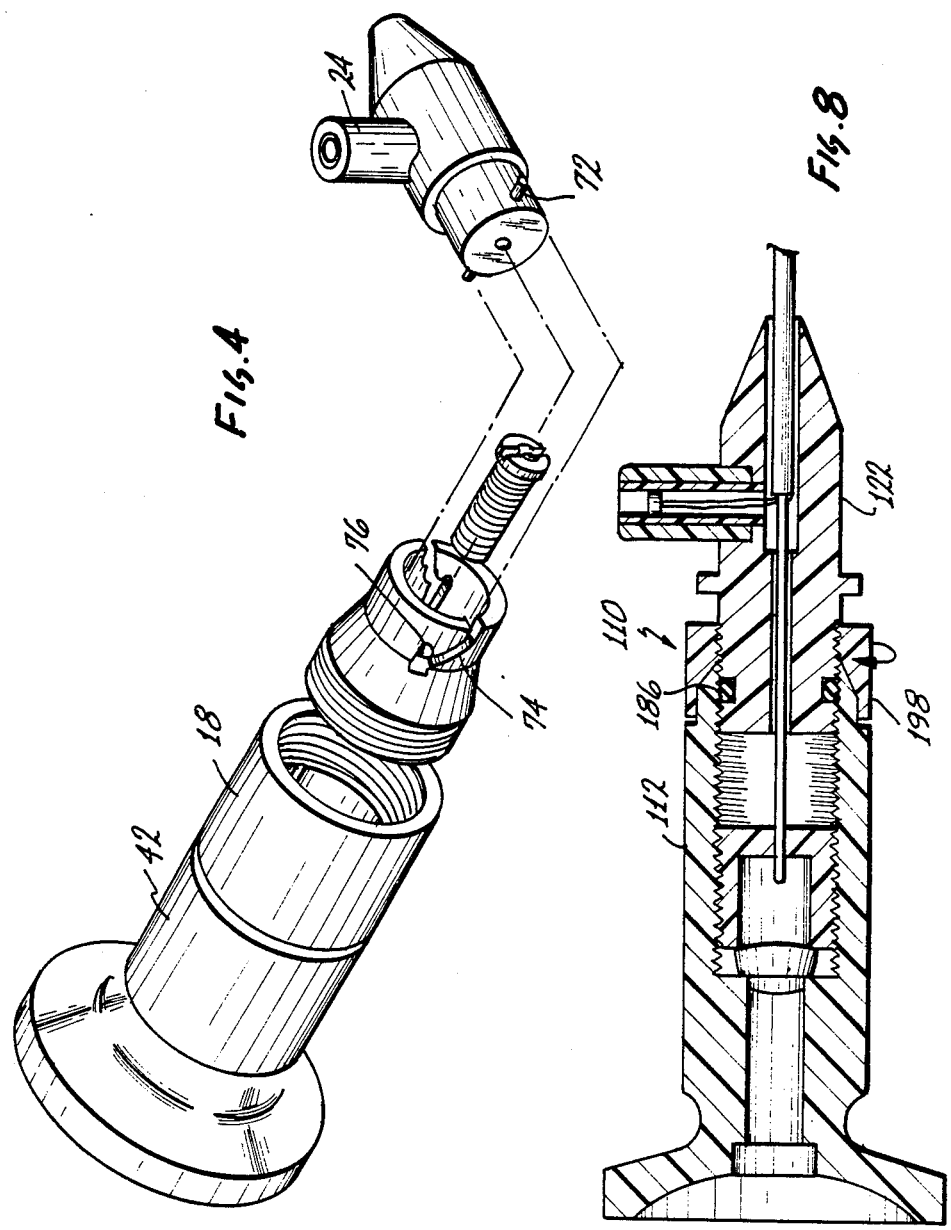

SOAKABLE EYEPIECE FOR ENDOSCOPES

FIELD OF THE INVENTION

This invention relates to endoscopes, and more particularly to an endoscope sterilizable by immersion into a liquid sterilant.

BACKGROUND OF THE INVENTION

In a hospital environment, sterilization is generally accomplished by one of three methods: 1) exposure to a sterilant gas; 2) steam autoclaving; or 3) immersion into a liquid sterilant. Because of the inability of some endoscope materials to withstand autoclaving temperatures, and because gas sterilization may be unavailable or impractical in some situations, it is desirable for an endoscope to be sterilizable by liquid immersion.

Unfortunately, prior art adjustable-focus endoscopes such as those shown in copending application Ser. No. 720,590 filed Apr. 8, 1985 and entitled "Disposable Small Diameter Rigid Endoscope" could not be liquid-sterilized because the liquid would seep into the lens cavity of the eyepiece through the adjustment mechanism and would become trapped therein. It was therefore desirable to create an immersible or soakable endoscope which was easy to adjust, as inexpensive as possible to manufacture, and capable of maintaining its adjustment under rough handling.

SUMMARY OF THE INVENTION

The present invention fulfills the objectives stated above by providing an optical adjustment mechanism for an endoscope which resists the penetration of liquid into the lens chamber by using an O-ring seal and very fine screwthreads to seal the adjustment mechanisms, and by using a sliding pin arrangement to hold the stop housing against relative rotation with respect to the eyepiece.

In addition to making the endoscope soakable, the mechanism of this invention has several other advantages. For one, it not only allows the eyepiece and stop housing to be made entirely of plastic (thereby saving cost), but it actually encourages the use of plastic for optimum performance. Secondly, it allows convenient one-handed adjustment of the endoscope. Thirdly, the containment of the light and image fiber entirely within the stop housing saves at least one light fiber connection, thereby increasing the light efficiency of the instrument. Fourthly, the O-ring seal provides a uniform resistance to turning the adjustment collar and prevents accidental misadjustment of the focus by rough handling. Fifthly, the uncemented mounting of the lens in the inventive arrangement makes the lens self-aligning and interchangeable. Sixthly, the ability to factory-adjust the throw of the mechanism allows considerable loosening of the manufacturing tolerance for the image fiber rod whose end must be cut and polished—a process in which it is very difficult and costly to maintain close tolerance. Seventhly, the inventive mechanism makes the endoscope soakable in both assembled (fully disposable) form and disassembled (non-disposable eyepiece) form. Eighthly, assembly of the eyepiece and stop housing requires no alignment because the image fiber rod is centered on the axis of the eyepiece.

It is thus the principal object of the invention to provide a liquid-impervious focus adjustment mechanism for endoscopes.

It is another object of the invention to provide a mechanism of the type described which is easy to adjust and resists misadjustment due to rough handling.

It is a further object of the invention to provide a mechanism of the type described which provides enhanced ease of manufacture and attendant cost savings.

BRIEF DESCRIPTION OF THE DRAWINGS

FIG. 1 is an axial vertical section of a urethral endoscope constructed in accordance with the invention, in assembled form;

FIG. 2 is an enlarged transverse vertical section of the catheter portion of the device along line 2—2 of FIG. 1;

FIG. 4 is an exploded view of an alternative embodiment of the invention;

FIG. 8 is a section similar to FIG. 7 but showing the device in the locked position.

DESCRIPTION OF THE PREFERRED EMBODIMENT

Figure 3:
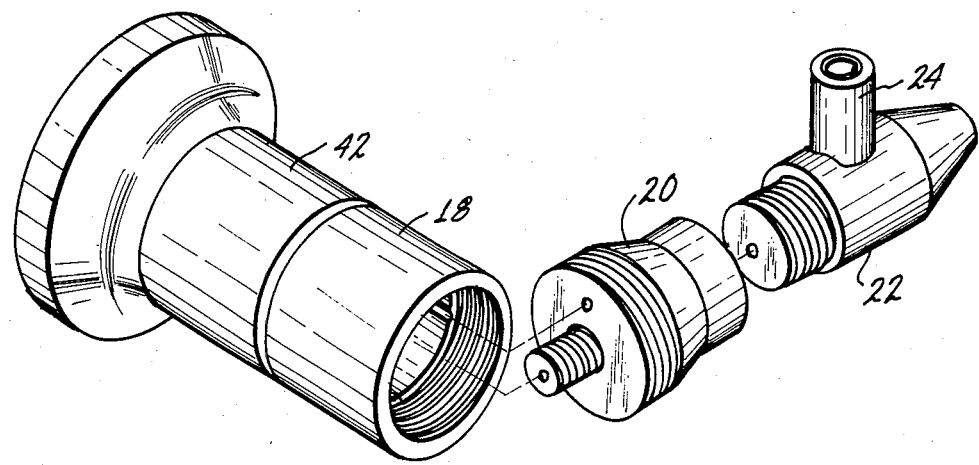
FIG. 3 is an exploded view of a preferred embodiment of the invention.

FIGS. 1 through 3 show a preferred embodiment of the invention. In these figures, the numeral 10 designates a urethral endoscope which consists of an eyepiece 12 including a lens chamber 14, an adjustment cavity 16, an adjustment collar 18, and a stop housing connector 20; a stop housing 22 including a light source connector 24; a conventional flexible fiber conduit 26; a conventional Y connector 28; and a conventional flexible multi-lumen urethral catheter 30 with an optical objective element 32 at its distal end.

In the manufacture of the eyepiece 12, a lens 40 is loosely inserted into the barrel 42 of the eyepiece 12 into which a plano 44 has previously been press-fitted, and the lens retainer 46 is screwed into the barrel 42. Next, the stop housing connector is aligned with the barrel 42 so that the pin 48 of the barrel 42 is coaxial with the pin guide opening 50 of the stop housing connector 20, and the adjustment collar 18, which has previously been screwed onto the stop housing connector 20, is slipped over the barrel 42 until it locks into place by the action of the snap ring 52. The stop screw 54 can now be loosely inserted into the recess 56 of the stop connector 20 and screwed into the lens retainer 46 to the desired depth. A gasket 58 is next inserted into the recess 60 of stop housing connector 20, whereupon the eyepiece 12 can be assembled with the stop housing 22.

In the embodiment of FIGS. 1 and 2, the stop housing 22 is assembled with the eyepiece 12 by screwing its threaded nose 62 into the threaded recess 60 of the stop housing connector 20 until the transverse face 64 of the nose 62 sealingly engages the gasket 58. In the embodiment of FIG. 4, the assembly is done by hooking a pair of pins 72 into guide slots 74 and twisting the stop housing 22 until the resiliency of the gasket 58 pushes the pins 72 into the lock recesses 76 of the guide slots 74.

In the assembly of eyepiece 12 and stop housing 22, by either method, the steel-sheathed end 66 of the image fiber 68 slips into the central bore 70 of stop screw 54 where it is held in alignment with lens 40.

In accordance with one aspect of the invention, the light source connector 24 is mounted on the stop housing 22 rather than on the eyepiece 12 as in the prior art. This construction has several advantages. First, it avoids a discontinuity in the light fibers 78, and the inevitable resulting loss of light efficiency; secondly, it avoids the need for rotational alignment of the stop housing 22 with the eyepiece 12 during assembly; and thirdly, the light source connector 24 provides a finger grip for the one-handed adjustment of the endoscope 10 as hereinafter described.

The endoscope 10 of this invention is focused by turning the collar 18 with respect to the eyepiece barrel 42. Because of the engagement of pin 48 with pin guide opening 50, the stop housing connector cannot rotate with respect to the eyepiece barrel 42 but can only translate in an axial direction. The leftward movement of the connector 20 in FIG. 1 is limited by its engagement with the shoulder 80 of the barrel 42, while its rightward movement is limited by the engagement of shoulder 82 of connector 20 with the head 84 of stop screw 54.

In the mechanism of this invention, the throw or range of movement of connector 20 is adjustable by screwing the stop screw 54 into or out of the lens retainer 42. This is a useful feature when using the eyepiece 12 with different lenses 40 or different stop housings 22 whose image fibers may terminate at different distances from the nose 62.

In the structure of FIGS. 1, 3 and 4, an O ring 86 serves the dual function of sealing the left end (in FIG. 1) of collar 18 against liquid penetration between collar 18 and barrel 42, and of offering a constant, soft frictional resistance to the turning of collar 18. This makes it easier to properly focus the endoscope 10, and the resilience of the O ring 86 allows the endoscope 10 to maintain its focus if the eyepiece 12 is dropped or otherwise carelessly handled.

The right end (in FIG. 1) of the collar 18 is sealed against liquid penetration between collar 18 and connector 20 by using a very fine screwthread (e.g. twenty or more threads per centimeter) where the collar 18 is screwed onto the connector 20. Due to the resiliency of plastic materials, it is advantageous to form the collar 18 and connector 20 (as well as all the other parts of the eyepiece 12 and stop housing 22) of plastic rather than metal. This is, of course, also a desirable thing to do from a standpoint of manufacturing cost. The seal between stop housing 22 and eyepiece 12 is provided by gasket 58.

In the device of this invention, it is practical to form the pin (or pins if more than one is provided) 48 as an integral part of barrel 42, because the stress imposed upon the pin 48 in order to prevent rotation of connector 20 is so much less than the stress imposed upon the guide pins of the prior art shown in the above-mentioned copending application Ser. No. 720,590 that it need not be made of metal.

Figure 5:
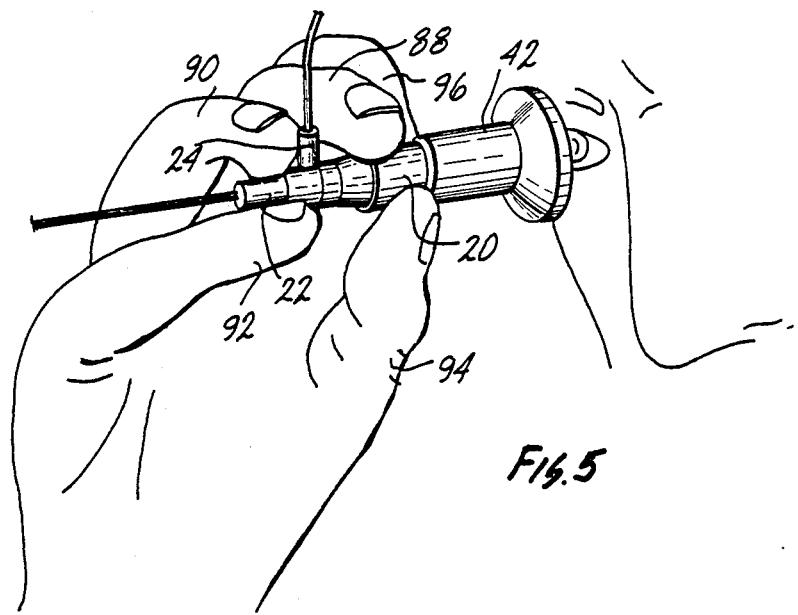
FIG. 5 is a perspective view showing the method of adjustment of the device of this invention.

FIG. 5 illustrates an advantage of the present invention which is produced by locating the light source connector 24 on the stop housing 22 rather than on the eyepiece 12. By positioning the middle finger 88 and the ring finger 90 on each side of the light source connector 24, and the little finger 92 underneath the stop housing 22, the collar 18 can easily be turned between the thumb 94 and index finger 96 while looking through the eyepiece 12, without rotating either the stop housing 22 or the eyepiece barrel 42.

Figure 7:
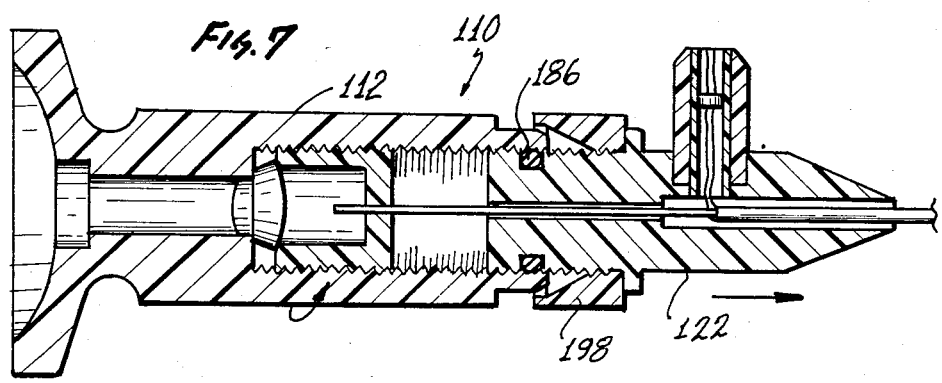
FIG. 7 is an axial vertical section of the device of FIG. 6 in the unlocked position.
Figure 6:
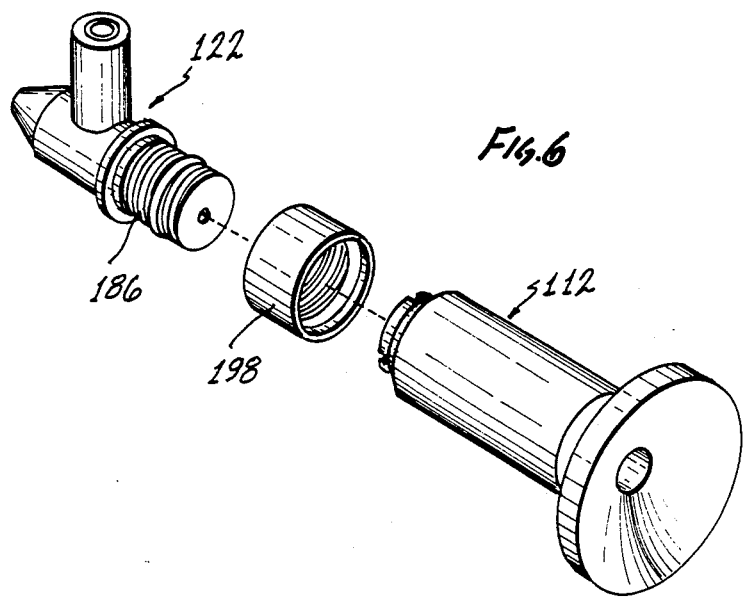
FIG. 6 is an exploded view of another alternative embodiment of the invention.

FIGS. 6 through 8 illustrate an alternative embodiment of the invention in which the focusing is done simply by screwing the eyepiece 112 more or less deeply onto the stop housing 122. An O ring 186 interposed between two adjacent sets of screwthreads on stop housing 122 provides the seal which allows soaking the endoscope 110 without fear of liquid penetration. The same turning resistance and immunity to rough handling are provided by O ring 186 as are provided by O ring 86 in the previously discussed embodiments. One-handed adjustment is also possible as shown in FIG. 5; however, in the embodiment of FIGS. 6 through 8, the eyepiece 112 would have to rotate with respect to stop housing 122 during adjustment.

A screwthreaded locking ring 198 is provided in the embodiment of FIGS. 6 through 8 to lock a focus setting against movement. In the position of locking ring 198 shown on FIG. 7, the focus of the endoscope 110 can be adjusted by rotating the eyepiece 112 with respect to the stop housing 122. After the proper focus setting has been made, the locking ring 198 is screwed toward the eyepiece 112 until it engages the eyepiece 112 and squeezes its threads to prevent further rotation.

We claim:

1. In an endoscope having an eyepiece including a barrel and a stop housing assembly movable axially but not rotatably with respect to each other, said eyepiece being focusable by axially moving said barrel and stop housing with respect to each other through rotation of a screwthreaded rotatable collar circumferentially surrounding at least a portion of said barrel and said stop housing assembly, the improvement comprising liquid-impervious sealing means interposed between said collar and said barrel and between said collar and said stop housing assembly for preventing liquid sterilant from penetrating between said barrel and said stop housing assembly.

2. The improvement of claim 1, in which said sealing means include screwthreads on said collar of sufficient firmness to form a liquid-tight barrier when engaged with corresponding threads on one of said barrel and stop housing assembly.

3. The improvement of claim 2, in which said sealing means further include an O ring interposed in frictional relationship between said collar and the other of said barrel and stop housing assembly.

4. The improvement of claim 3, in which said collar is retained on said barrel so as to allow rotary movement but not axial movement of said collar with respect to said barrel, and said collar is screwthreadedly retained on said stop housing assembly so as to allow both rotary movement and corresponding axial movement of said stop housing assembly with respect to said collar.

5. The improvement of claim 4, in which said collar is retained on said barrel by a split ring positioned between said O ring and said screwthread sealing means.

6. The improvement of claim 1, in which relative rotary movement between said barrel and said stop housing assembly is prevented by slidable engagement of a pin on one of said barrel and stop housing assembly with a pin guide opening on the other of said barrel and stop housing assembly.

7. The improvement of claim 6, in which said pin is formed integrally with said one of said barrel and stop housing assembly.

8. The improvement of claim 1, in which said stop housing assembly includes a stop housing connector axially but not rotatably movable with respect to said barrel, and a stop housing coaxially engageable therewith.

9. The improvement of claim 8, in which said coaxial engagement is a screwthreaded engagement.

10. The improvement of claim 8, in which said coaxial engagement is a pin-and-slot engagement.

11. The improvement of claim 8, further comprising gasket means interposed between said stop housing and said stop housing connector for preventing liquid from penetrating into the interior of said stop housing connector.

12. The improvement of claim 8, in which said stop housing connector has an interior cavity formed therein, and said barrel has a screw coaxially mounted thereon, the head of said screw being engageable with a wall of said cavity by sufficient axial movement of said stop housing connector away from said barrel.

13. The improvement of claim 12, in which the axial movement of said stop housing connector is limited in one direction by engagement of said connector with said barrel, and in the other direction by engagement of said screw head with said all of said cavity.

14. The improvement of claim 1, in which said barrel includes a lens, and a lens chamber mounted coaxially within said barrel, said lens being so shaped as to be aligned into coaxiality with said barrel by the mounting of said lens chamber into said barrel.

15. The improvement of claim 1, in which said barrel includes a plano, said plano being press-fitted into said barrel.

16. The improvement of claim 3, in which the frictional engagement between said O ring, said collar, and said one of said barrel and stop housing assembly is such that said O ring offers a substantially constant sliding resistance to rotary movement of said collar with respect to said one of said barrel and stop housing assembly.

17. The improvement of claim 1, in which said barrel and stop housing assembly are relative axially movable between adjustable limits.

18. In an endoscope having an eyepiece assembly including an eyepiece member having an annularly rotatable adjustment collar, and a stop housing releasably attachable to said eyepiece member, said stop housing having therein an image fiber for observation from said eyepiece member, and at least one light fiber for transmission of light into said endoscope from a light source connected to a light fiber connector, the improvement comprising placing said light fiber connector on said stop housing in such a position with respect to said eyepiece as to allow one-handed rotation of said collar while grasping said stop housing at said light fiber connector with the same hand, so as to prevent rotation of said eyepiece when adjusting said endoscope one-handedly.

19. A soakable eyepiece assembly for an endoscope, comprising:
  a) an eyepiece member;
  b) a stop housing coaxially attachable to said eyepiece member by a screwthreaded connection having two spaced screwthreaded portions; and
  c) an O ring positioned between said portions, said O ring forming a liquid-tight seal between the interior of said eyepiece member and said stop housing while allowing relative rotary and corresponding axial movement between said eyepiece member and stop housing.

20. The assembly of claim 19, further comprising locking collar means arranged to selectively lock said eyepiece member with respect to said stop housing by compressing said eyepiece member and stop housing together.

21. An endoscope comprising:
  an eyepiece assembly including an eyepiece barrel having a viewing port;
  a distal section including an elongated body adapted to be at least partially received within a patient, said body having a distal end;
  first light-conducting means for conducting light from said eyepiece assembly to adjacent the distal end of the body;
  second light-conducting means for conducting an image from adjacent the distal end of the body to the viewing port, said second light-conducting means including a lens in said barrel and an elongated light conductor at least partially in said body and having a proximal end lying distally of the lens; and
  focusing means for relatively adjusting the relative axial position of the lens and the proximal end of the light conductor;
  said focusing means including a focusing collar, means for mounting the focusing collar for rotation without translation and means responsive to rotation of the focusing collar to adjust the relative axial position of the lens and the proximal end of the light conductor;
  the light conductor being movable axially with the body, said focusing means including means for threadedly coupling the focusing collar and the body and means for holding the body against rotation whereby rotation of the focusing collar moves the body and the light conductor to adjust the relative axial position of the lens and the light conductor; and
  said means for holding said body against rotation including a pin extending in an axial direction from one end of said barrel and body, said pin extending into a pin guide opening formed in the other of said barrel and body.

* * * * *